(12) United States Patent
Uutela et al.

(10) Patent No.: US 8,574,156 B2
(45) Date of Patent: Nov. 5, 2013

(54) DETERMINATION OF THE CLINICAL STATE OF A SUBJECT

(75) Inventors: Kimmo Uutela, Helsinki (FI); Matti Huiku, Espoo (FI); Juha Virtanen, Helsinki (FI)

(73) Assignee: General Electric Company, Helsinki (FI)

( * ) Notice: Subject to any disclaimer, the term of this patent is extended or adjusted under 35 U.S.C. 154(b) by 1078 days.

(21) Appl. No.: 11/174,763

(22) Filed: Jul. 5, 2005

(65) Prior Publication Data

US 2007/0010723 A1    Jan. 11, 2007

(51) Int. Cl.
*A61B 5/00*  (2006.01)
*A61B 5/0476*  (2006.01)
*A61B 5/04*  (2006.01)
*G06F 19/00*  (2011.01)

(52) U.S. Cl.
CPC .......... *A61B 5/0476* (2013.01); *A61B 5/04001* (2013.01); *A61B 5/04004* (2013.01); *A61B 5/7275* (2013.01); *A61B 5/7282* (2013.01); *A61B 5/0006* (2013.01); *G06F 19/34* (2013.01); *G06F 19/3431* (2013.01); *Y10S 128/92* (2013.01)
USPC ............. 600/301; 600/300; 600/544; 702/19; 128/920

(58) Field of Classification Search
USPC .................... 600/300, 301; 128/903–905, 920
See application file for complete search history.

(56) References Cited

U.S. PATENT DOCUMENTS 5,458,117 A * 10/1995 Chamoun et al. ............. 600/547
5,906,208 A *  5/1999 Ishikawa et al. .............. 128/898
6,016,444 A *  1/2000 John ............................. 600/544
6,120,443 A *  9/2000 Cohen-Laroque ............ 600/300
6,265,978 B1 * 7/2001 Atlas ............................ 340/575

(Continued)

FOREIGN PATENT DOCUMENTS

EP    0 553 162    5/1997
EP    1 273 265    1/2003

(Continued)

OTHER PUBLICATIONS

Linkens et al., "Clinical implementation of advanced control in anaesthesia", The Institute of Measurement and Control, 0142-3312(00)TM019OA, 2000.

(Continued)

*Primary Examiner* — Bill Thomson
*Assistant Examiner* — Marie Archer
(74) *Attorney, Agent, or Firm* — Andrus, Sceales, Starke & Sawall, LLP

(57) ABSTRACT

The invention relates to the determination of the clinical state of a subject. A respective adaptive transform is applied to at least one measurement signal acquired from the subject, each adaptive transform being dependent on previously acquired history data, and a diagnostic index is formed, which is dependent on the transformed measurement signal(s) and serves as a measure of the clinical state of the subject. In order to reliably evaluate the clinical state of a subject on a fixed diagnostic scale during changes in the state of the subject, some or all of the previously acquired history data on which an adaptive transform is currently dependent is replaced with other previously acquired history data when a predetermined event is detected. The predetermined event is indicative of a change in the respective measurement signal, and the introduction of the said other previously acquired history data sets the transform ready for the change.

16 Claims, 8 Drawing Sheets

(56) References Cited

U.S. PATENT DOCUMENTS

| | | | |
|---|---|---|---|
| 6,315,736 B1* | 11/2001 | Tsutsumi et al. | 600/500 |
| 6,658,287 B1 | 12/2003 | Litt et al. | |
| 6,685,649 B2* | 2/2004 | Korhonen | 600/485 |
| 6,801,803 B2 | 10/2004 | Viertio-Oja | |
| 7,215,994 B2* | 5/2007 | Huiku | 600/544 |
| 7,447,541 B2* | 11/2008 | Huiku et al. | 600/544 |
| 8,028,694 B2* | 10/2011 | Hickle | 128/203.14 |
| 2004/0111041 A1* | 6/2004 | Ni et al. | 600/544 |
| 2004/0158295 A1 | 8/2004 | Dyjach et al. | |
| 2004/0193068 A1* | 9/2004 | Burton et al. | 600/544 |
| 2005/0010116 A1 | 1/2005 | Korhonen et al. | |
| 2005/0143617 A1* | 6/2005 | Auphan | 600/26 |

FOREIGN PATENT DOCUMENTS

| | | |
|---|---|---|
| WO | WO-2004/034897 | 4/2004 |
| WO | 2004/112603 A1 | 12/2004 |
| WO | 2005018737 A1 | 3/2005 |

OTHER PUBLICATIONS

European Search Report dated Sep. 22, 2011.

* cited by examiner

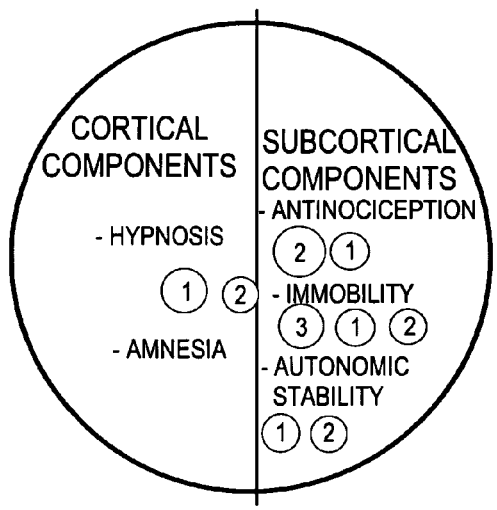
FIG. 1
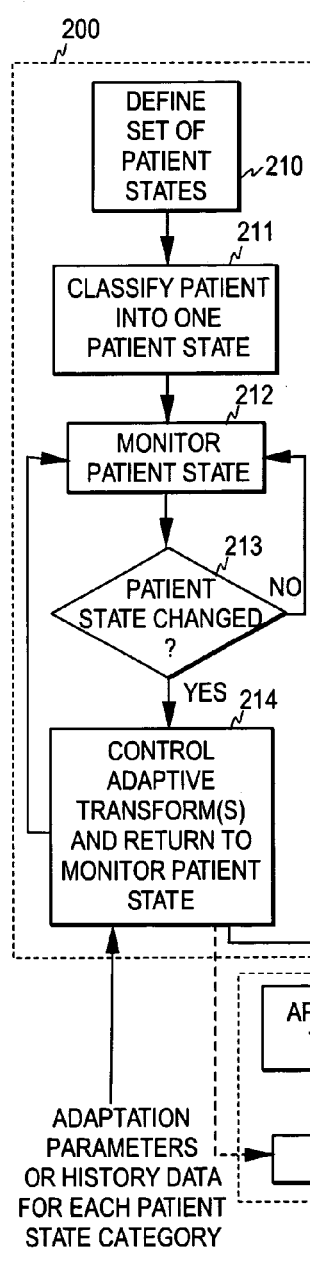
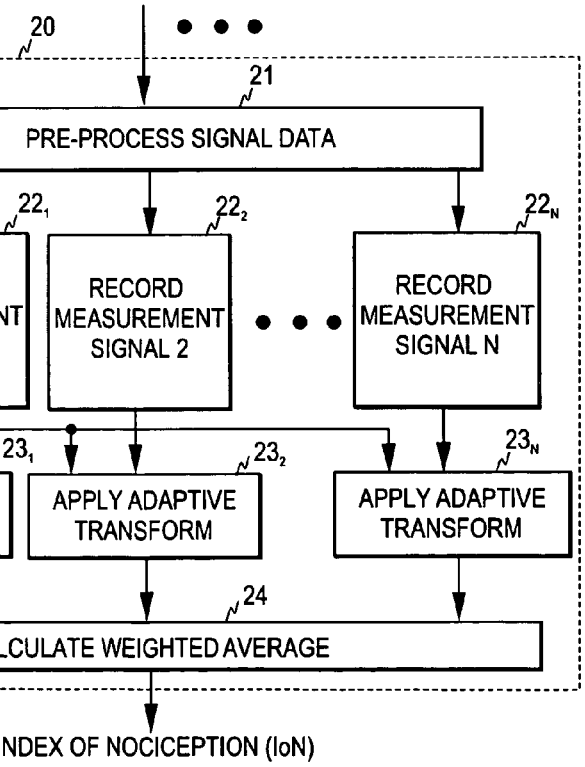
FIG. 2

Group Average

Individual Patient Distribution

Partially Adapted Patient Distribution

Cumulative Patient Distribution

Parameter Value

DETERMINATION OF THE CLINICAL STATE OF A SUBJECT

FIELD OF THE INVENTION

The present invention relates generally to the determination of the clinical state of a subject. One application of the invention is the determination of the nociceptive or antinociceptive state of a subject.

BACKGROUND OF THE INVENTION

Pain is an unpleasant sensory or emotional experience that is associated with actual or potential tissue damaging stimuli. It is always an individual and subjective sensation, which may be acute (nociceptive), elicited by noxious stimuli, or chronic pain that has outlived its usefulness to preserve tissue integrity. The perception of pain takes mainly place at cortex, and it may be suppressed in deep sedation and anesthesia by the general (global) inhibitory effects of sedative drugs and anesthetic agents. The responses to noxious stimulus may also be suppressed when the pain signal pathway is sufficiently suppressed at the subcortical level, often in the region of the brainstem and spinal cord. Both cortical and subcortical mechanisms play a role in pain management in modern surgical anesthesia or intensive care.

Analgesia refers to absence of pain or loss of sensitivity to stimulation that would normally be painful. Analgesic state is independent of the level of consciousness of the patient.

Noxious stimuli, such as pin pricks or inflammation exceeding a certain threshold stimulus level in nociceptive nerve fibers (nociceptors), cause a nociception, i.e. a neuronal signal or perception that denotes the induced pain or injury. Nociception is transmitted in the Central Nervous System (CNS) via several different ascending pathways causing responses that can be cortical pain responses or subcortical stress responses. NSAIDs (Non-Steroidal Anti-Inflammatory Drugs) effectively relief pain at a damaged tissue site, whereas opioids selectively affect the pain pathways in the region of the spinal cord or the brainstem. Local or regional anesthetic agents, for instance those used in epidural analgesia, block both the pain and the sensory pathways in the spinal cord region.

Antinociception normally refers to the blocking or suppression of nociception in the pain pathways at the subcortical level. It may be described as subcortical analgesia, in distinction to preventing the perception of pain at the cortex, i.e. cortical analgesia.

The autonomic nervous system (ANS) is the 'unconscious' nervous system, which controls and regulates virtually all of our basic body functions, such as cardiac function, blood circulation and glandural secretion. The main parts of the ANS are the parasympathetical and sympathetical nervous branches. The sympathetical nervous system usually prepares us for high stress situations by speeding up the body functions. Under conditions of normal ANS regulation, the parasympathetical system restores the normal conditions in blood circulation by slowing down the heart rate. Pain, discomfort, and surgical stress may activate the sympathetical branch of the ANS and cause an increase in blood pressure, heart rate, and adrenal secretions.

Neuromonitoring is a subfield of clinical patient monitoring focused on measuring various aspects of brain function and on changes therein caused by drugs commonly used to induce and maintain anesthesia in an operation room or sedation in patients under critical or intensive care.

Electroencephalography (EEG) is a well-established method for assessing brain activity by recording and analyzing the weak biopotential signals generated in the cortex of the brain with electrodes attached on the skin of the skull surface. The EEG has been in wide use for decades in basic research of the neural systems of the brain, as well as in clinical diagnosis of various neurophysiological diseases and disorders.

Electromyography (EMG) is a method for recording electrical biopotentials of muscles. In an EMG measurement, the electrodes are attached on the surface of the skin at a muscle group. An EMG signal is often recorded from the skull of the patient, whereby the recorded signal indicates both the activity of the facial muscle (fEMG) and the brain (EEG). As the frequencies of the EMG spectrum are usually high and above the frequencies of brain activity, the signal components can be separated by methods of signal processing or spectral analysis from the EEG signal.

Electrocardiography (ECG) is another well-established method for assessing cardiac function by recording and analyzing the biopotential signals generated in the heart. Electrodes are attached on the skin of the chest with more peripheral references. The ECG is commonly used for diagnosing cardiac dysfunctions, various cardiac and circulatory diseases, and arrhythmias. Heart rate (HR), often derived from the ECG waveform, is one of the most important parameters characterizing the condition of a patient.

Respiration rate is another vital sign, which is often monitored even in basic patient care. In connection with anesthesia and sedation of ventilated patients, monitoring of the respiration is often combined with monitoring of gas exchange, which includes monitoring of inhaled and exhaled oxygen, carbon dioxide and anesthetic gases. In modern gas monitors, airway pressure (AWP) and gas flows are also measured in order to improve the safety and quality of the ventilation.

Blood pressure (maintaining blood circulation) is yet another vital sign obtained from a patient. It may be monitored either non-invasively (NIBP) or invasively (InvBP) using catheters inserted in the arteries or veins. The latter techniques are continuous and they allow a detailed monitoring of the regulation of the cardiac-circulatory and pulmonary functions.

Pulse oximetry is a well-established technique for measuring oxygen saturation (SpO2) in arterial blood. SpO2 is an important parameter, nowadays often called as the fourth vital sign, which relates to the adequacy of oxygen supply to peripheral tissues and organs. Pulse oximeters also display a photoplethysmographic (PPG) pulse waveform, which can be related to tissue blood volume and blood flow, i.e. the blood circulation, at the site of the measurement, typically in finger or ear. The amplitude of a PPG waveform is a sensitive indicator of patient discomfort and pain, but it also reacts to non-noxious stimulations.

Analysis methods using the heart rate variability (HRV) are emerging techniques for diagnosing cardiac diseases, such as lack of oxygen supply to the cardiac muscle, and for characterizing the cardiac function and the condition of the patient in general. Fast changes in the heart rate are usually caused by the parasympathetical ANS control mediated in the vagal cranial nerve. Vagal control slows down the heart beat. The slow variations (<0.15 Hz) of the heart rate are mainly associated with sympathetical activity, which accelerates the heart beat. The ratio of the fast components of the HRV to the slow components of the HRV is often called the sympatho-vagal balance, which in emergency or during intense surgical stress turns to sympathetical dominance.

During the past few years, several commercial devices for measuring the level of consciousness and/or awareness in a clinical set-up during anesthesia have become available. These devices, which are based on a processed one-channel EEG signal, have been introduced by Aspect Medical (Bispectral Index), by Datex-Ohmeda (Entropy Index), and by Danmeter (an auditory evoked EEG potential monitoring device, AAI™). At present, the situation with the assessment of the cortical activity and integrity is considered satisfactory, though not resolved for all applications.

As to the central nervous system (CNS), the assessment or measurement of the suppression of the sub-cortical activity, the ANS and the integrity of subcortical evaluations is far more unsatisfactory. No commercial devices exist for this purpose. This is mainly because the sub-cortical components are not represented in any single bioelectrical or other signal, in contrast to that the EEG almost alone may represent the cortical activity. The monitoring of the adequacy of anesthesia or sedation thus—in addition to monitoring the hypnotic state of brains by EEG—call for a multi-parameter approach, which combine parameters describing the overall responsiveness of the patient to "unconscious" stimulations. This may be defined by means of the hemodynamic, motor, and endocrine stability. A promising basis for searching a multi-parameter monitoring method for sub-cortical activity may thus possibly be found from the subtle features in the common vital signs, the heart rate, the respiration rate, the blood circulation, and the blood pressure.

The sub-cortical integrity of the afferent input, ANS evaluations, and efferent autonomic output is best researched in unconscious subjects with noxious stimulations and their responses, as these are mainly processed and modulated in the brainstem and spinal levels. The responses can also be modulated (attenuated) by analgesic or antinociceptive drugs, which influence the pain pathways at the sub-cortical levels. A successful monitoring method shall thus demonstrate a clear relationship and correlation between both the effect of the analgesics on the suppression of the nociceptive responses and the intensity of the noxious stimulations on the strength or amount of the responses in the parameters.

The need for reliable monitoring of the adequacy of anesthesia is based on the quality of patient care and on economy related aspects. Balanced anesthesia reduces surgical stress and there is firm evidence that adequate analgesia decreases postoperative morbidity. Awareness during surgery with insufficient analgesia may lead to a post-traumatic stress disorder. Prolonged surgical stress sensitizes the central pain pathways, which post-operatively increases patient pain and secretion of stress hormones. Low quality pre- and intra-operative analgesia makes it difficult to select the optimal pain management strategy later on. More specifically, it may cause exposure to unwanted side effects during the recovery from the surgery. Too light an anesthesia with insufficient hypnosis causes traumatic experiences both for the patient and for the anesthesia personnel. From an economical point of view, too deep an anesthesia may cause increased perioperative costs through extra use of drugs and time, and also extended time required for post-operative care. Too deep a sedation may also cause complications and prolong the usage time of expensive facilities, such as the intensive care theater.

U.S. Pat. No. 6,801,803 discloses a method and device for ascertaining the cerebral state of a patient. In this disclosure, a measure derived from EMG signal data enhances and confirms the determination of the hypnotic state made using EEG signal data. As the EMG data may be computed more frequently than the EEG data, this renders ascertaining changes in the hypnotic state of the patient more rapid. In this method, the (facial) EMG thus alone reflects the suppression of the nociceptive pathways. State entropy (SE), which is calculated in the low frequency band up to 32 Hz, is dominated by the cortical EEG activity, while response entropy (RE), which also includes the high frequencies, represents both the cortical and muscle activity. The difference RE-SE is, therefore, a measure of the (f)EMG power, which will increase at nociception and which, therefore, may be a good measure of the suppression of the pain pathways. However, the above-mentioned dependency on the medication of the patient may render the method unusable in certain situations. As the (facial) electromyography signal is affected by neuro-muscular blocking agents (NMBAs), which suppress signaling at the nerve-muscle junctions, the EMG component of the measurement may vanish and render the method unusable, if the medication of the patient includes neuro-muscular blocking agents. It shall also be emphasized that the difference RE-SE is not specific to the suppression of the pain pathways but also reflects the overall motoric activity following any arousals—that is, emotional or normal sensory evoked arousals, too. For instance, when the patient is awake and not perceiving any pain or discomfort, the RE-SE difference is typically about 8-10 per cent. At deep hypnosis it is obvious that only painful stimulations can cause RE to differ from SE, but it is difficult to tell at which level the transition to the only-nociception induced varying difference in the deep anesthetia takes place.

EP Patent 0553162 (corresponding to U.S. Pat. No. 5,372, 140) proposes a method and apparatus for assessing the depth of anesthesia by using respiratory sinus arrhythmia (RSA) as a measure of the state of the brain. The document describes a method in which a parameter indicative of clustering of the heart beat pattern is determined from the ECG waveform relative to the beginning of each respiration cycle. This parameter is then compared with a reference value calculated using a test for randomness. The parameter is then compared with the reference value to derive a measurement of the depth of anesthesia. In particular with spontaneously breathing anesthetized patients, the clustering is proportional to the RSA, which decreases with deepening anesthesia. The heart rate changes influencing the clustering are primarily controlled by the parasympathetical branch of the ANS, and therefore, the depth of anesthesia is related to the parasympathetical activity. This, however, correlates poorly with sympathetical effects, i.e. with the pain and nociception, and therefore also poorly with the adequacy of analgesia. Furthermore, the clustering takes place differently in artificial over-pressure ventilation and in spontaneously breathing patients, as the heart rate always accelerates during the low pressure period of the respiration cycle and decelerates during the high pressure phase. The low pressure period occurs during the inspiration in case of spontaneously breathing patients and during the expiration in case of artificial ventilation. The proposed method works reasonably well for spontaneously breathing patients, who in addition have a large RSA, such as children, but often fails in connection with artificially ventilated older patients. Pain reduces RSA amplitudes, as does the deepening of anesthesia. As a result, a low value of clustering may suggest too deep an anesthesia, leading to a decrease in the level of hypnosis. This may, however, lead to a worse situation, as a result of which the patient may even wake up, especially if surgical stimulations are intense.

U.S. Pat. No. 6,120,443 also suggests a method based on a heart beat interval (ECG R-to-R peak interval, RRI) analysis to assess the depth of anesthesia. In this method, the degree of randomness of the heart beats is described by means of a fractal dimension of the series of the R-R Intervals, mathematically describing the correlation within the RRI series.

High correlation is indicative of a low fractal dimension and of only very few (CNS) processes, which add irregularities in the RRI series. Low correlation and thus high randomness equals high fractal dimension, which implies that the anesthesia is light and that many processes influence the RRI series. The methods for calculating the fractal dimensions are computationally heavy. In addition, the suggested method suffers from the fact that the degree of both hypnosis and analgesia affect the fractal dimension. The orthogonality of the two measures corresponding to the cortical and subcortical activity is thus poor. Although the method was primarily suggested for measuring the hypnosis of the patient, it is probable that it will also correlate with the degree of the surgical stress, which increases hemodynamic instabilities and the fractal dimension of the RRI series. Using this method, it is thus difficult to tell, which type of a drug, an opioid or a hypnotic, is primarily needed, and whether the drug concentration should be added or reduced.

European patent application EP 1273265 (corresponding to U.S. Pat. No. 6,685,649) describes a simpler method for analyzing an RRI and a blood pressure (BP) time series. Furthermore, the method tries to make a clear distinction between the sympathetical and parasympathetical cardiovascular responses. The sympathetical responses correlating with the surgical stress increase the heart rate and blood pressure. The acceleration index of the heart rate and the index for the increase of the blood pressure is calculated using a filter, a kind of edge filter, which detects the increasing slopes in the values of RRI or BP, but neglects the decreasing values. The document suggests that these indices may be used as a measure of the adequacy of analgesia. However, the method lacks the specificity to noxious stimuli and detects also the variations caused by respiration and other increasing slopes resulting from normal sympathetical activation without noxious stimulation. For instance, when the patient is in light anesthesia, both the sympathetical and parasympathetical branch of the ANS is active and the indices show erroneously high values suggesting insufficient analgesia.

The above prior art technologies thus aim to describe the adequacy of anesthesia using a unidimensional concept for the depth of anesthesia. They do not account for separate hypnotic and analgesic components, which are orthogonal, i.e. as much independent of each other as possible, and specific to the hypnotic and analgesic medications given during anesthesia. Thus the prior art methods cannot not answer to the question, whether one should add or reduce the analgesics or hypnotics in order to restore a balanced anesthesia. All prior art technologies that are claimed to measure the adequacy of analgesia show a considerable dependence on the level of hypnosis and, consequently, at light anesthesia without any noxious stimulations show a value that is usually associated with poor analgesia. A further drawback of the prior art technologies is that the measurement values show a considerable inter-patient variability. This makes their interpretation, i.e. the interpretation of the adequacy of anesthesia, difficult.

International patent application WO 2004/034897 (corresponding to U.S. Published Application 2005/0143665) discloses a method and an apparatus for a plethysmographic based detection of nociception during anesthesia and sedation. In this method, predetermined pulse wave parameters are detected and compared with reference values obtained earlier by measuring the same parameters over a certain preceding time window. If a substantial change is detected in at least one pulse wave parameter, preferably in waveform amplitude, a change in another pulse wave parameter, preferably the position of the dicrotic notch, is determined. If both changes are substantial, the changes are displayed or recorded and interpreted as an indication of a nociceptive event. The method thus provides an indication of the presence of noxious stimulation. Since the method is based on detection of noxious events, i.e. short-lived changes in the signal, it cannot provide an indication of the basic level of antinociception. In other words, the relative balance between the analgesic drug effect and the level of noxious stimulation cannot be estimated or measured, which makes the method unsuitable for automatically controlling the delivery of analgesic drugs.

U.S. Patent application 2005/0010116 discloses a method and an apparatus for monitoring the condition of a patient under anesthesia or sedation. In this method, a mathematical index for probability of patient comfort is calculated. The probability index is obtained as a combination of physiological parameters extracted from a plethysmographic waveform, an ECG waveform, and/or EMG power measured from patient forehead. Again, as in the above-referred WO application 2004/034897, the parameters in the probability index are referred to a certain reference value determined over a certain time window or at certain reference event. Since the index is only indicative of the probability of nociception, it cannot provide quantitative information of the level of nociception or of changes in the said level. Therefore, this algorithm is also unsuitable for automatically controlling the delivery of analgetics.

The present invention seeks to eliminate or alleviate the above drawbacks and to accomplish a novel and quickly adaptive mechanism for obtaining a quantitative measure of the clinical state, especially of the level of nociception, of a patient.

SUMMARY OF THE INVENTION

The present invention seeks to provide a novel mechanism for monitoring the clinical state of a subject. The clinical state here refers to a physiological status of the subject, which is indicative of a need or effect of a treatment or intervention, where the term physiological relates to physiology, the science dealing with the functions of living matter and beings. The present invention further seeks to provide a mechanism that allows fast adaptation of the measurement to a change in the statistical properties of the physiological signal(s) on which the measurement is based.

In the present invention, at least one measurement signal is acquired from the subject, each measurement signal being indicative of a respective physiological parameter. An adaptive transform is then applied to each of the measurement signals, and the diagnostic index is formed based on the output signal(s) of the transform(s). An adaptive transform here refers to an operation adapted to convert an input value to an output value and provided with an input-output relationship that depends on previously acquired signal data, here also termed history data. The occurrence of one or more predetermined events is monitored, which indicate a change in the statistical properties of one or more of the physiological signals on which the measurement is based, and thus also in the input signal of at least one adaptive transform. A predetermined event may be, for example, a change in the state of the subject, such as the transition of the subject from a wake state to a sleep state. Upon detection of such an event, the adaptative transforms whose input signals are affected are controlled to replace some or all of the history data, on which the said transforms are currently dependent, with other history data.

Since the techniques used to implement the adaptive transforms may vary, the replacement of the underlying history data on which a transform is currently dependent may be carried out in various ways. For example, desired parameters may be derived from the history data, in which case new parameter values are introduced upon detection a predetermined event. The new parameter values are derived from history data which is partly or wholly different than the history data from which the replaced parameter values were derived. In some implementations, separate parameters may not need to be derived from the history data, but the history data itself may act as the information setting the transform ready for the change in its input signal. The transforms are thus dependent on underlying history data, either directly or indirectly, and upon detection a predetermined event at least part of the underlying history data on which the input-output relationship of a transform depends is replaced with other history data.

The history data may be acquired before or during the current measurement session. The said other history data may thus be acquired in advance for the change situations, by measuring corresponding input signal data from the same subject or from a group of other subjects similar to the subject. Furthermore, all the history data on which an input-output relationship depends is not necessarily changed at once, but the history data on which the input-output relationship depends after the predetermined event may include part of the history data on which the input-output relationship depended prior to the said event.

Upon detection a predetermined event, the adaptivity of the measurement is thus improved by instructing each adaptive transform in whose input signal a statistical change has occurred or is about to occur to change its adaptation mechanism. As a result, at least part of the history data on which the transform is currently dependent is replaced with other history data in which the statistical change may already be seen and which thus sets the transform ready for the change.

As indicated above, the replacement of the underlying history data may involve instructing the relevant transform to introduce new adaptation parameters derived from the history data acquired for the change in question. As a result of this, the said transform starts to use the new adaptation parameters which are indicative of the statistical properties of the input signal after the change, and which thus set the transform ready for the change.

In one embodiment of the invention, the measurement signal to which an adaptive transform is applied is produced by combining a plurality of signals indicative of respective physiological parameters. In this embodiment, the output of the adaptive transform forms the diagnostic index indicative of the clinical state of the subject, whereas in other embodiments employing several parameter signals the diagnostic index is produced based on the transformed signals.

Thus one aspect of the invention is providing a method for determining the clinical state of a subject. The method includes the steps of acquiring at least one measurement signal from the subject and subjecting at least one of the at least one measurement signal to at least one adaptive transform, respectively, whereby at least one transformed measurement signal is obtained, wherein each adaptive transform is dependent on previously acquired history data. The method further includes the steps of forming a diagnostic index, which is dependent on the at least one transformed measurement signal and serves as a measure of the clinical state of the subject, and replacing at least part of the previously acquired history data on which at least one of the at least one adaptive transform is currently dependent with other previously acquired history data, the replacing step being performed when a predetermined event is detected.

In one embodiment, a plurality of subject state categories may be defined in advance and the subject may be classified into at least one category based on his or her current state. One or more adaptation parameters may be attached to each adaptive transform for each subject state category, whereby the adaptation parameter(s) of a particular subject state category define the transform to be performed after the category of the subject has changed to said particular category.

In a typical application of the invention, in which the nociceptive state of a subject is determined, the physiological signal(s) or parameter(s) obtained from the subject is/are indicative of the cardiovascular function of the subject, especially of a pulsative component of a peripheral blood circulation of the subject, since changes in the pain state of the subject are reflected in the said signals or parameters. However, the physiological signal(s) or parameter(s) obtained from the subject may be any other signals or parameters indicative of the physiological feature pertaining to which the clinical state is to be determined.

Another aspect of the invention is that of providing an apparatus for determining the clinical state of a subject. The apparatus includes measurement means for acquiring at least one measurement signal from the subject and transform means for subjecting at least one of the at least one measurement signal to at least one adaptive transform, respectively, thereby to obtain at least one transformed measurement signal, wherein each adaptive transform is dependent on previously acquired history data. The apparatus further includes means for forming a diagnostic index which is dependent on the at least one transformed measurement signal and serves as a measure of the clinical state of the subject, first monitoring means for detecting a predetermined event, and control means for replacing at least part of the previously acquired history data on which at least one of the at least one adaptive transform is currently dependent with other previously acquired history data, the control means being responsive to the first monitoring means.

The solution of the invention provides a fast adaptive mechanism for monitoring the clinical state of a subject. Furthermore, the invention provides a sensitive mechanism for detecting changes, such as noxious events, which occur immediately after the subject state has changed.

A further aspect of the invention is that of providing a computer program product by means of which known measurement devices, such as pulse oximeters, may be upgraded to enable monitoring of the clinical state of the subject. The program product includes a first program code portion configured to receive at least one measurement signal and a second program code portion configured to subject at least one of the at least one measurement signal to at least one adaptive transform, respectively, thereby to obtain at least one transformed measurement signal, wherein each adaptive transform is dependent on previously acquired history data. The program product further includes a third program code portion configured to produce a diagnostic index which is dependent on the at least one transformed measurement signal and serves as a measure of the clinical state of the subject, a fourth program code portion configured to detect a predetermined event, and a fifth program code portion configured to replace at least part of the previously acquired history data on which at least one of the at least one adaptive transform is currently dependent with other previously acquired history data, the fifth program code portion being responsive to the fourth program code portion.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 11 in the appended drawings, wherein:

FIG. 1 illustrates the concept of the quality of anesthesia;

FIG. 2 is a flow diagram illustrating the determination of the index of nociception in one embodiment of the invention;

DETAILED DESCRIPTION OF THE INVENTION

Figure 3:
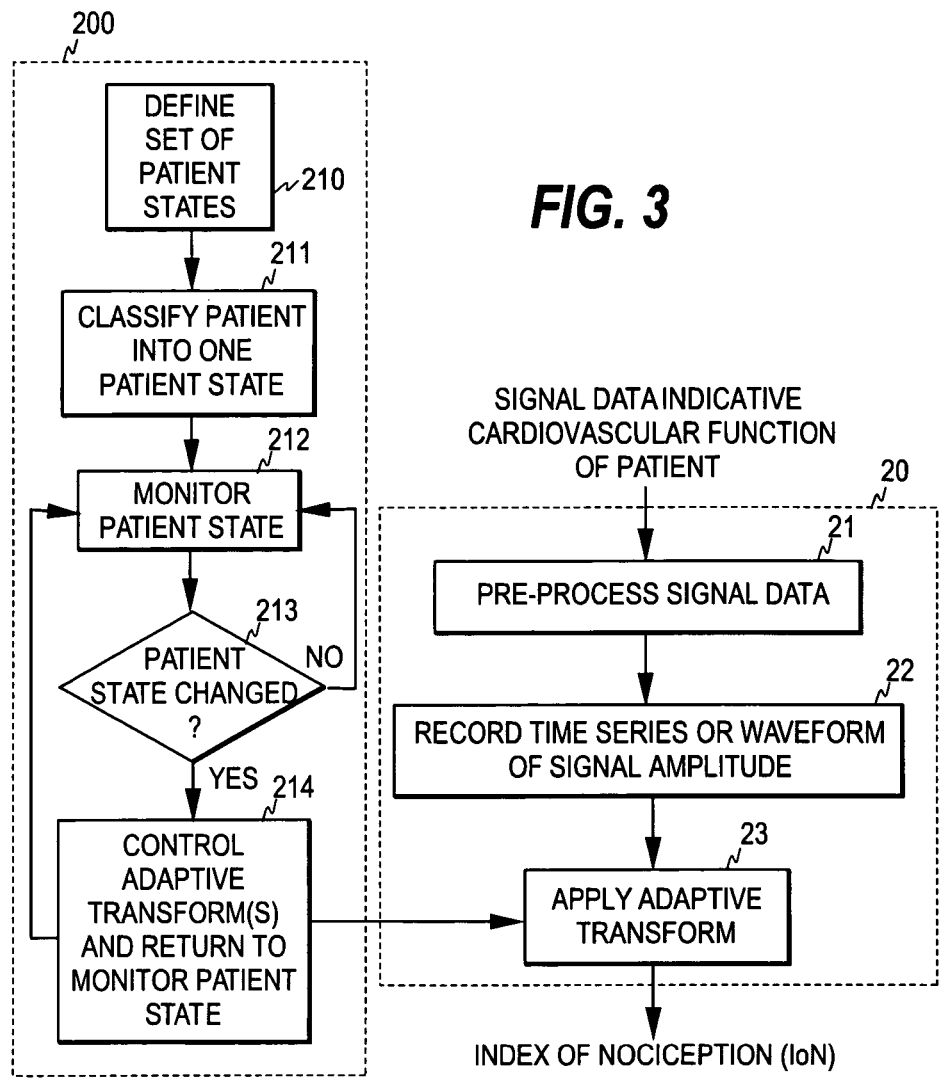
FIG. 3 illustrates an embodiment, in which the index of nociception is determined based on one physiological parameter.

Below, the invention is described more specifically by referring first to embodiments pertaining to the determination of the antinociceptive component of anesthesia in a patient.

FIG. 1 illustrates the concept of the quality of anesthesia. According to the current comprehension, the quality of anesthesia includes five different components: hypnosis (i.e. unconsciousness), amnesia, antinociception, immobility, and the stability of the ANS. The first two components, the hypnosis and amnesia, are of cortical origin and are indicative of cortical activities and processes. The suppression of the cortical activity is obtained by drugs, which typically affect neural signaling globally in the brain. The drugs may activate the natural inhibitory GABA (gamma-aminobutyric acid) receptor system in the brains or prevent, by an unknown mechanism, neural signaling in the synapses between the neurons. For this reason, the drugs often also affect other parts than the cortex in the brain, thereby also suppressing subcortical activity and processes.

The other components in the anesthesia model, which are indicative of sub-cortex related activity in the patient, are much more specific and often relate to altering, modulating or blocking neural signaling at certain receptor or neurotransmitter level. These components can be affected selectively by different specific drugs. For instance, antinociception, i.e. the suppression of the neural transmission in the pain pathways, is achieved by opioid drugs, which affect the opioid/enkephalin receptors and activate the descending pathways, which block or modulate the nociceptive stimuli in the spinal cord. Furthermore, the NMBA drugs block the neural transmission in peripheral neuromuscular junctions, which results in one kind of specific immobility of a patient. The stability of the ANS and the antinociception are closely related, since noxious stimulation in deep anesthesia causes hemodynamic and hormonal instability. The stability of the ANS is therefore also advanced by opioid drugs and by several other drugs, which may affect specifically the parasympathetical or sympathetical activities of the ANS.

FIG. 1 also shows the drugs associated with each component of the anesthesia model by showing numbered circles, in which number one refers to hypnotics, number two to opioids, and number three to NMBAs. Although many drugs may be involved in achieving an adequate level of the cortical and subcortical activity, the adequacy of anesthesia is often managed only by a gas anesthetic agent or other hypnotic agent, which dominantly (and globally) affects the cortical activity, by an opioid, which selectively modulates the pain pathways at subcortical level, and by a NMBA drug, which induces immobility by blocking neuronal transmission in peripheral nerve-muscle junctions. The effects of the hypnotic agent may be monitored, for instance, by the above-described methods based on calculation of spectral entropy and the neuromuscular blockade by an NMT (NeuroMuscular Transmission) measurement. The hypnotic and NMBA drugs can then be administered based on these measurements.

Pain-related responses may be monitored by detecting changes in the activity of the sympathetical branch of the ANS of the patient. For this purpose, sympathetical responses, i.e. short-lived signal changes which eventually return back to the base level of the signal, may be counted in a certain fixed time window, and pain may be detected if the rate of accepted responses exceeds a certain threshold value. To determine an appropriate threshold value for accepted response counts, the physiological signal involved may be normalized. Although this mechanism allows pain-related responses to be monitored, it does not provide quantitative information of the level of nociception or of changes in the said level.

A quantitative measure of the current clinical state of a patient may be obtained by generating a measure of the said state directly based on a measurement signal containing desired physiological information obtained from the patient. This may be implemented by applying to said signal a normalization transform, which is dependent on predetermined history data, such as previous data of the said measurement signal. This allows the measurement to adapt to the patient in question, i.e. the patient-to-patient variability in the measurement signal values may be eliminated. The state of the patient may thus be evaluated on a diagnostic scale, such as a nociception scale, on which a certain reading corresponds to the same level for all patients.

However, the state of the ANS may change abruptly when the patient falls asleep or wakes up. For example, the patient may be nervous while awake, and inhibiting the cortical control may abruptly change the ANS. Therefore, the physiological signals or parameters on which the measurement is based may change substantially as a result of the change in the patient state. When these signals or parameters are used to generate a measure of the clinical state of the patient, the measurement must first adapt to the new signal or parameter values of the patient before it reliably reflects the clinical state of the patient.

The present invention provides a novel mechanism which enables the monitoring of the trend of the clinical state, such as the level of nociception, of a patient, and which also enables fast adaptation to changes that affect the signals or parameters based on which the clinical state is determined.

FIG. 2 illustrates one embodiment of the present invention, in which an index of nociception is formed. The embodiment of FIG. 2 may be divided into two parts: a measurement part 20 comprising the actual measurement of the clinical index and a control part 200 controlling the measurement part based on the state of the patient.

A set of patient state categories is first established for all patients, the set including at least two state categories in which a patient may be during the treatment (step 210). Below, the patient state category is also termed the subject state category, since the method may also be used in a non-hospital environment. Since the present example relates to the determination of the index of nociception, the patient states relevant in this context are indicative of the level of hypnosis in the patient. It is thus assumed here that the set includes two state categories, a wake state category indicating that the patient is awake (conscious) and a sleep state category indicating that the patient is in sleep (unconscious). The patient is then classified into one of these state categories (step 211). For example, before a surgery the patient is conscious and is thus classified into the wake state category. The state of the patient is continuously monitored to detect when the patient moves to another patient state category, i.e. in this case the patient is monitored to detect the transition to the sleep state category (step 212).

The transition between the sleep and wake state categories may be detected, for example, by measuring the EEG of the patient and determining an index of hypnosis based on the EEG signal. The index of hypnosis may be determined similarly as in the above-mentioned U.S. Pat. No. 6,801,803. In other words, at step 212 a parameter may be defined, which characterizes the amount of disorder or complexity in the EEG signal data obtained from the patient. Currently, the use of spectral entropy is deemed advantageous for this purpose due to the computational simplicity as compared to the other techniques available. However, other quantifications, such as fractal spectrum analysis, Lempel-Ziv complexity or bispectral or multispectral analyses may also be used for this purpose. As a more detailed discussion of the various mathematical techniques available for obtaining such a parameter can be found in the above-referred patents, these methods are not discussed in detail in this context.

Thus, at step 212 the state of the patient may be monitored based on a continuous determination of the hypnosis index of the patient. A predetermined threshold value defined for the hypnosis index may then indicate that a transition to the sleep state category has occurred. At step 213, the hypnosis index is compared with the predetermined threshold value and if the threshold is reached, the adaptive transforms are controlled (step 214) to adapt each transform to the change in the statistical properties of the input signal, which occurs when the patient falls asleep. As discussed below, in this embodiment the control is carried out by introducing new adaptation parameter values derived from the history data acquired for the transition in question.

Simultaneously with the above steps, the physiological signal data is measured from the patient in order to define the index of nociception based on the said data. As discussed below, the physiological signals which may be employed for this purpose include a plethysmographic signal, such as a photoplethysmographic (PPG) signal, a blood pressure (BP) signal, an ECG signal, or a Laser Doppler flow signal in peripheral tissues. This due to the fact that changes in the nociceptive state of the patient may be seen in these signals.

The measurement of the signal waveform data of each physiological signal may be implemented in a conventional manner, i.e. while the patient connected to a patient monitoring system, the signal waveform data is recorded and stored in a memory of a monitoring device. In order for the method to be quick enough, the measurement is such that new signal values are received frequently, for example at about 100 samples/sec.

The recorded waveform data of each physiological signal may be pre-processed at step 21 for filtering out some of the frequency components of the signal or for rejecting artifacts, for example. This step, which is not necessary and may be performed to improve the quality of the signal data, may be different for each physiological signal.

Next, the desired feature, i.e. parameter, indicative of nociception is extracted from the signal data at steps $22_1 \ldots 22_N$. It is assumed in the example of FIG. 2 that a set of N (N=1, 2, ...) measurement signals are generated at this stage, whereby N time series are obtained, each representing the desired feature in the corresponding physiological signal. These steps may involve, for example, the extraction of pulse amplitude or the pulse-to-pulse interval for each pulse beat. As is shown in the figure, the N measurement signals may be obtained based on 1 to N physiological signals. This is due to the fact that one or more physiological parameters may be derived from one physiological signal.

Each time series is then subjected to an adaptive transform, which scales the input signal values to a predetermined output value range (steps $23_1 \ldots 23_N$). The transform applied to each input signal is further adaptive in the sense that it adapts to the signal data of the patient in question. The transformed signal values are then combined at step 24 to form a composite indicator that serves as the index of nociception. This may be performed by continuously calculating a weighted average of the N transformed signal values obtained at each time from the N time series.

The weighted average thus forms the index of nociception, which is indicative of the level of (anti)nociception in the patient. However, the index is not necessarily updated as frequently as a new output value is obtained, but the index may be calculated, for example, as an average over a certain number of output values output from the transform.

If the index of nociception is determined in the above-described manner using the steps of the measurement part 20 only, the measurement may be insensitive immediately after the change to the sleep state occurs. This is because such a change may cause a substantial change in the level of the measurement signal(s). The adaptation to the new values takes some time and during this adaptation time the measurement may be insensitive to changes in the nociceptive state of the patient. The above is due to the fact that when the patient is awake the state of the ANS may be substantially different from what it is when the patient under anesthesia (i.e. unconscious). For example, both before and after anesthesia the heart rate and the amplitude of a plethysmographic signal may be at levels which during the anesthesia would indicate strong noxious stimulation. Therefore, the measurement may be incapable of differentiating between normal values of a wakeful patient and exceptional values of an anesthetized patient before the measurement has had time to adapt to the new values obtained from the anesthetized patient. To eliminate this possibility, the adaptation mechanism is changed when the change in the patient state occurs or is about to occur. This is discussed in the following.

When the state of the patient changes so that he/she is to be classified to another state category, each transform to whose input signal the change affects is controlled to change the respective adaptation mechanism. In each patient state category, the adaptive transform(s) may utilize a set of adaptation parameters, which describe desired statistical properties, such as mean and standard deviation, of the corresponding measurement signal in that patient state category. As discussed below, the adaptation parameters may be determined from the same patient or from a patient group.

The adaptation mechanism may be changed by instructing each adaptive transform to introduce the adaptation parameters that correspond to the new patient state category. In other words, a set of adaptation parameters may be attached to each patient state category. Thus, in this example each adaptive transform is provided with a first parameter set for the wake state category and a second parameter set for the sleep state category. Each set may include, for example, at least one statistical measure describing the input signal in the corresponding category, such as the mean value and the standard deviation of the input signal values in the sleep state category.

In one embodiment of the invention, several adaptation parameter sets may be attached to one patient state category. For example, several adaptation parameter sets may be determined for the sleep state category, each set corresponding to a certain medication which may be used to anesthetize the patient. Thus, when the patient falls asleep, the parameter set is selected, which pertains to the sleep state category and corresponds to the medication of the patient. As obvious from the above, the said selection is made for each transform.

The adaptation parameter sets needed by each transform may be stored in conjunction with the transform, whereby the controlling at step 214 may only involve sending of a notification including an identifier identifying the adaptation parameter set to be taken into use.

In order to obtain the adaptation to the patient in question, the adaptive transform may be made dependent on time series data recorded previously for the same patient. For example, the adaptive transform may be dependent on the mean and variance of the input signal, which are defined based on data measured earlier during a measuring period of a predetermined length, such as 3 minutes, or from a certain event to the present, such as since the beginning of the surgery. As sleep state data is normally not available for the patient when the patient falls asleep, the initial phase of the sleep state may be based on data measured previously from a corresponding patient group.

A further feature of the adaptive transform is that it may emphasize slow changes in the input signal. This is accomplished by making output values that correspond to the mean or center of the input value range relatively more sensitive to input value changes than the values in the tail regions. This mechanism enhances small changes or trends in the input values and damps large, jump-like responses in the input signal. The transform is thus especially suitable for detecting relative slow changes, i.e. trends, in the patient status, such as drug affected changes in the level of antinociception.

By using different adaptation mechanisms for anesthetized (unconscious) and wakeful patients noxious events may be detected more accurately when the change occurs and during the period which is normally needed to adapt to the new parameter values obtained from the patient.

Above, it was assumed that N (N=1, 2, 3, . . . ) measurement signals are derived from 1 to N physiological signals measured from the patient. FIG. 3 illustrates an embodiment of the invention, in which N equals one. In this embodiment, the index of nociception is formed by means of one measurement signal, and the output of the adaptive transform directly forms the index of nociception. The adaptive transform is controlled by the control part 200 as discussed above. The physiological signal employed in this case is indicative of the function of the cardiovascular system of the patient, since changes in the level of nociception are reflected in such signals. Possible signals include a plethysmographic signal, such as a photoplethysmographic (PPG) signal, a blood pressure (BP) signal, an ECG signal, or a Laser Doppler flow signal in peripheral tissues.

The cardiovascular system includes the heart, veins, arteries, and blood. Its main function is to transport oxygen and nutrients to all areas of the body and carry away carbon dioxide to the lungs and other wastes to the kidneys for excretion. The functions of the cardiovascular system induce a plurality of physiological signals that may be recorded to obtain information of the cardiovascular status of the subject. Such physiological signals include signals indicative of the peripheral blood circulation of the subject, such as a plethmysmographic signal or a blood pressure signal. Blood pressure pulsation caused by the beating heart or air pressure variations in the lungs, for example, are mediated to the peripheries of the body through the vascular system. The tone of the vascular system regulates the conduction of the pulsation. Changes in the vascular tone form an independent source of pulsation detected in the peripheries of the body. Typical peripheral locations for the recording of the pulsation are finger tips and ear lobes. Therefore, most of the signals indicative of the function of the cardiovascular system, such as a PPG signal, a BP signal, or a Laser Doppler flow signal are also indicative of the pulsative component of the peripheral blood circulation.

The parameter recorded at step 22 of FIG. 3 is preferably the pulse amplitude. The amplitude is extracted for each pulse beat from the signal data, whereby a time series of the amplitude of the pulsative component of the peripheral blood circulation is obtained. This time series is supplied as an input signal to the adaptive transform.

The specificity of the index of nociception to noxious stimulation and to analgesic drug concentration may be improved by adding the number of parameters based on which the index of nociception is formed, i.e. by increasing the value of N from one.

Figure 4:
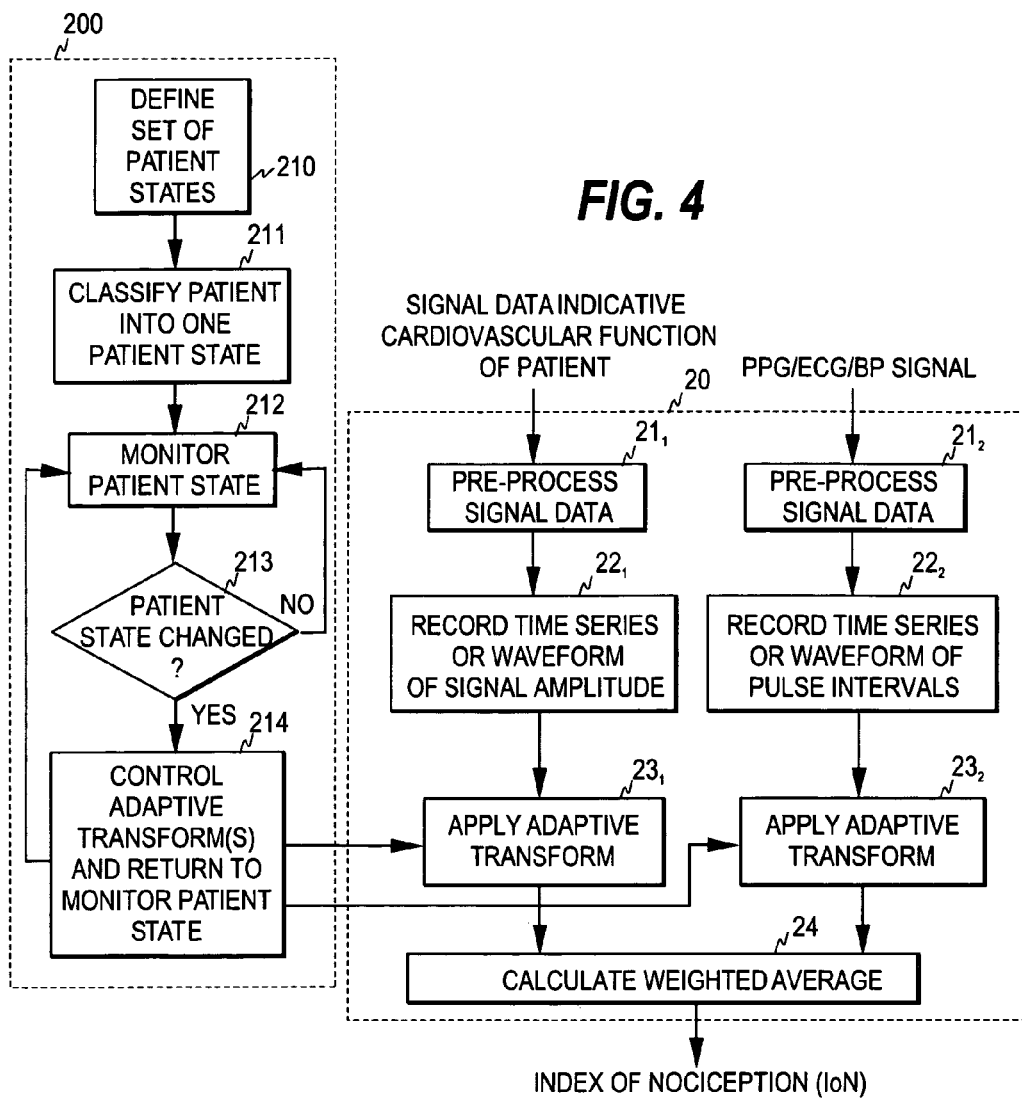
FIG. 4 illustrates an embodiment, in which the index of nociception is determined based on two physiological parameters.

FIG. 4 illustrates an embodiment of the invention, in which N equals two. In this case, the time domain is taken into account by producing the composite indication, i.e. the weighted average, based on the signal of the embodiment of FIG. 3 and a second transformed time series, which is in this case indicative of pulse interval. The pulse interval here refers to the beat-to-beat interval of the physiological signal in question. The physiological signal(s) may be a plethysmographic signal, an ECG signal, and/or a blood pressure signal. As either a plethysmographic signal or a blood pressure signal may be used to obtain the transformed pulsative component at step $23_1$, the same signal data may be used to derive the time series of the pulse interval. Thus, in this case the signal may be supplied from step $21_1$ directly to step $22_2$, in which the time series of the pulse interval is generated. However, if the two measurement signals are based on different physiological signals, a pre-processing step $21_2$ similar to step $21_1$ may precede step $22_2$.

In an embodiment in which a PPG signal is employed, the weighted average WA may be calculated, for example, as follows:

WA=−(0.33*RRI(norm)+0.67*PPGA(norm))+100, where RRI refers to the pulse-to-pulse interval, PPGA refers to PPG amplitude, and norm refers to normalized parameter values.

Figure 5:
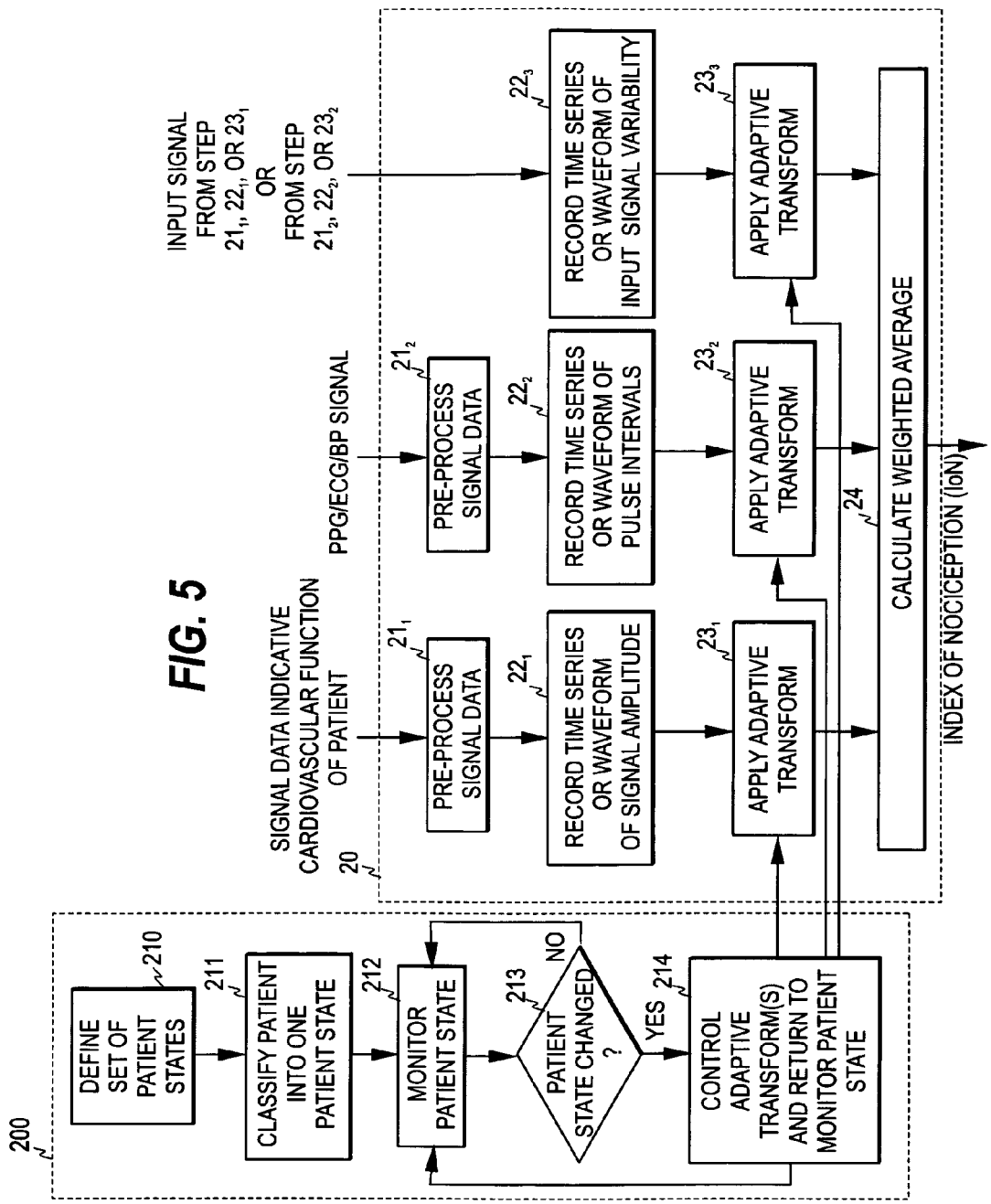
FIG. 5 illustrates an embodiment, in which the index of nociception is determined based on three physiological parameters.

FIG. 5 illustrates an embodiment of the invention, in which N equals three. The third parameter employed in this case may be indicative of the variability of either the first or the second transformed signal or the corresponding non-transformed signal. The input signal to the input branch corresponding to the third parameter may thus be supplied from any of steps $21_1$ to $23_1$ if the variability of the first measurement signal is utilized or from any of steps $21_2$ to $23_2$ if the variability of the second measurement signal is utilized. A time series or waveform of the third parameter is then produced at step $22_3$ by calculating, based on the input signal, a parameter which is indicative of the variability in the input signal. If the input signal is the pulse interval, the parameter calculated may be, for example, the ratio of the low frequency variability to the high frequency variability, i.e. the so-called sympatho-vagal balance, or a ratio similar to the sympatho-vagal balance. If the input signal is the pulsative component, the parameter calculated may be, for example, the power of respiratory variability.

It is also possible to use more than three parameters for the determination of the index of nociception by adding new physiological signals and/or by deriving new normalized signals from the physiological signals already employed.

The adaptive transform may be accomplished by any adaptive system, which is able to transform the input signal to an output signal which has the desired value range and desired distribution characteristics. Such a system may be implemented by various techniques, which include the use of a parameterized function transform or the use of a so-called histogram transform, for example.

The adaptive transform may also be implemented by a Kalman filter or by a neural network, for example. The use of the parameterized function transform and the histogram transform are described in the following.

Figure 6:
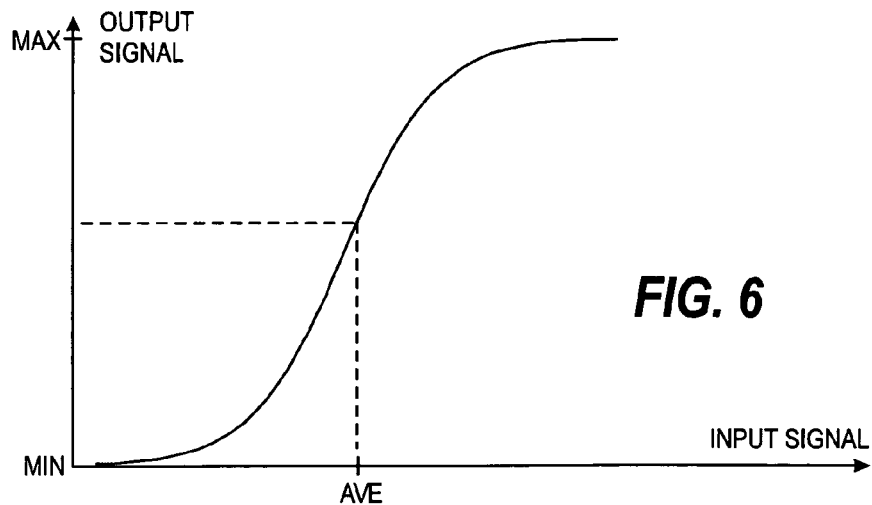
FIG. 6 illustrates an example of the input-output characteristics of the adaptive transform.

FIG. 6 illustrates typical input-output characteristics of an adaptive transform. The curve of a typical function transform corresponds to a sigmoid function, i.e. the output value y depends on the input value x according to equation (1):

$$y = \frac{A}{1 + e^{-B*x}}, \quad (1)$$

where A and B are adaptation parameters. As discussed below, A is typically a positive constant determining the scale of the index values, while B may be a patient-specific parameter, which determines the distribution of the output index values within the scale from zero to A. The two adaptation parameters are determined for each patient state category.

As can be seen from the figure, the transform forces the input signal to a predetermined output value range between a minimum value MIN and a maximum value MAX. For Eq. (1), MIN equals to 0, while MAX equals to A.

The adaptation to the patient may be accomplished by defining one or more patient-specific adaptation parameters and making the transform dependent on the said parameter(s). For example, the mean <x> and standard deviation σ of the input signal may be determined prior to the surgery based on the time series data measured during measuring period of a predetermined length, such as 3 minutes. Since such a determination may normally be made only for the wake state, a priori information of the patient-specific parameters in the sleep state is not normally available before the transition to the sleep state occurs during the surgery. Therefore, parameters measured from a corresponding patient group may be used as the initial parameters for the sleep state. As mentioned above, the patients in the said corresponding patient group may have one or more features similar to the patient, such the medication, age group, and gender. Furthermore, the parameters obtained from the corresponding patient group may be modified according to the wake state parameters of the patient and the said patient group. For example, if the wake state parameters obtained from the patient indicate that the mean value is slightly greater as compared to the wake state mean value of the patient group, it is likely that about the same relationship is true in the sleep state.

The adaptive transforms of the wake and sleep state categories may then be made dependent on the adaptation parameters determined for the respective patient states. For example, parameter B may be set to a value equal to the inverse of the standard deviation, i.e. B=1/σ, and the input value x may be set to a value corresponding to the difference of the current input value $x_i$ and the mean value AVE, i.e. $x=x_i-AVE$, i.e. the input value may also be dependent on previous signal data.

An alternative function to Eq. (1) may be a cumulative distribution function of the Gaussian (normal) distribution function as depicted in Eq. (2):

$$f(X) = \frac{1}{\sigma\sqrt{2\pi}} \int_{-\infty}^{X} e^{-\frac{(x-<x>)^2}{2\sigma^2}} dx. \quad (2)$$

The emphasis of the slow changes may be accomplished by making the transform such that the slope of the transform curve is steepest around the input values that are most common, i.e. around the mean value AVE.

In the above-described manner, the time series input to the adaptive transform may be transformed to a surrogate signal that has a predetermined value range and predetermined distribution characteristics for all patients. When the patient is awake, the transform(s) use the adaptation parameters of the wake state category and upon receiving the information that the patient has fallen asleep, the transform(s) start(s) to use the parameters of the sleep state category. The initial parameter(s) used in the sleep state may be the sleep state parameter(s) measured from the corresponding patient group, or the said sleep state parameter(s) modified according to the relationship between the wake state parameters of the said patient group and the patient in question. The initial adaptation parameters may then be updated by gradually giving more weight to the patient-specific values of the same parameters, which are measured since the transition to the current patient state.

Figure 7A:
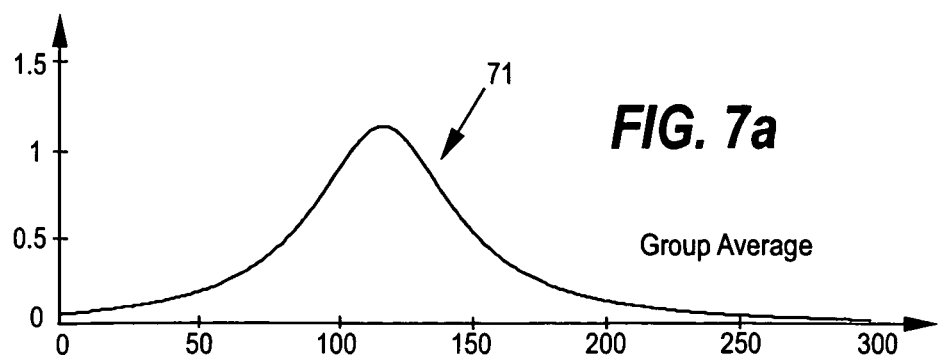
FIG. 7a to 7d illustrate one embodiment of the transform process of the invention.
Figure 7B:
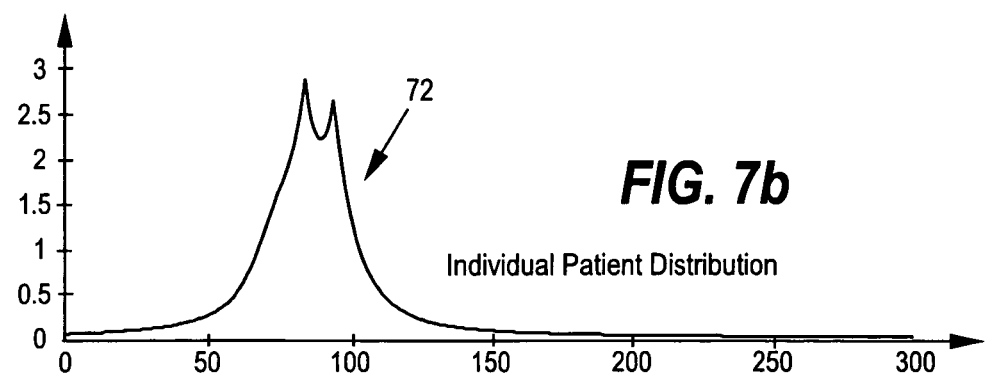

An adaptive transform may also be achieved by using a histogram transformation in steps 23. An embodiment of the histogram transformation is illustrated in FIG. 7a to 7d. FIG. 7a illustrates an a priori parameter distribution curve 71 obtained from a large number of patients representing a certain patient group in general anesthesia.

During the surgery the same parameter, such as the pulse-to-pulse interval, is measured and a histogram distribution is created. An example of a patient-specific distribution curve 72 obtained during a surgery is presented in FIG. 7b. The speed of the adaptation may be adjusted by, for example, setting a smaller weight or omitting data that is older than a predefined period, such as 30 minutes.

Figure 7C:
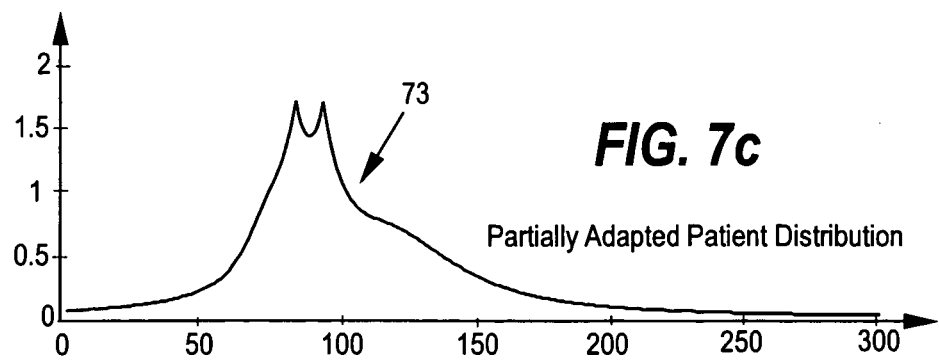

An a posteriori distribution may be created, for example, as a weighted sum of the two histograms, as shown in FIG. 7c. Another possibility is to increase the weight of the measured distribution as more data is available; this procedure may be viewed as a Bayesian estimate of the distribution of the parameter.

Figure 7D:
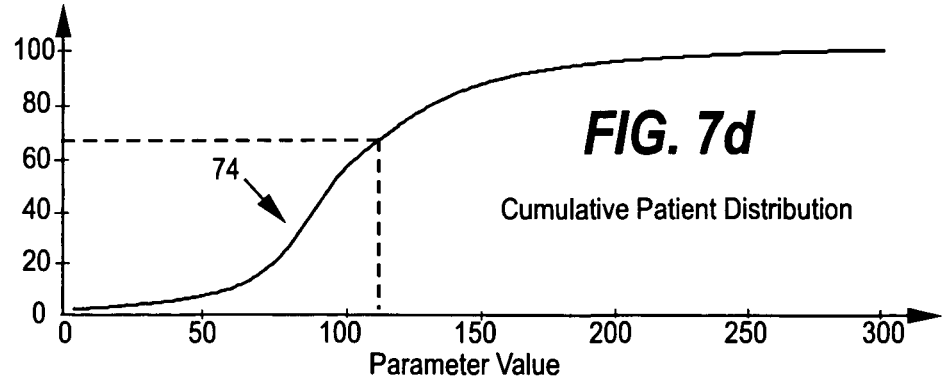

The distribution of the parameter values may be transformed to a uniform distribution from 0 to 100 per cent by applying the cumulative distribution function of the histogram (FIG. 7d).

If another distribution, such as normal distribution, is preferred, it may be obtained by applying the inverse cumulative distribution function of the desired distribution.

As a special case of the histogram transformation, a fully adaptive transform may be generated by using only the individual patient distribution. A patient group adaptive transform may also be generated by using the a priori distribution only. It is advantageous to use different distributions for different states of the subject also in case of a patient group adaptive transform.

Above, the invention was described in connection with embodiments pertaining to the determination of a nociceptive or antinociceptive index. However, as human variability is a common problem relating to all physiological measurements and as the relative effect of different physiological features varies on a patient-to-patient basis, the invention may be utilized to improve adaptation and sensitivity in connection with the determination of any diagnostic index indicative of a desired clinical state of the patient. For example, in the method described in the above-mentioned U.S. Pat. No. 6,801,803, in which a diagnostic index indicative of the cerebral state of the patient is calculated, the transform may be used in the above-described manner before the complexity measures forming the components of the diagnostic index are calculated. Similarly, adaptive transforms may be used to in connection with the determination of any diagnostic index, which is determined based on one or more physiological parameters or signals indicative of the physiological state in question. The patient states determined for a particular diagnostic index may also vary, and different patient states may be employed in connection with different diagnostic indices. The classification of the patient into different patient state categories may also be hierarchical, i.e. there may be several patient state categories within a particular patient state category. For example, in a heart surgery, the patient state categories may include the categories of "heart pumping" and "heart stopped" within the sleep state category, if there is a change in the statistical properties of the signal input to the transform when the heart is stopped during the surgery.

In the above-described embodiments, the adaptation mechanism is changed in response to a change of the patient state category into which the patient is to be classified. However, the onset of anesthesia may be detected in different ways. For example, the anesthesiologist may perform a manual selection, which indicates a change in the patient state. Furthermore, various other events related to the onset of anesthesia may give such an indication. Such events include the beginning of the ventilation and the beginning of the induction of anesthetic drugs, for example. Thus, instead of monitoring the hypnosis index the occurrence of various other events may be monitored to detect that the patient state category has changed or is about to change. Depending on the event monitored, a delay of predefined length may be added between the detection of the event and the change of the adaptation mechanism(s).

In a further embodiment of the invention, the calculation of the weighted average may also be changed when the adaptation mechanism is changed. This is indicated by a dashed arrow in FIG. 2. Thus in this embodiment both the adaptation mechanism and the index determination process are changed in response to a predetermined event, such as the change of the patient state category into which the patient is to be classified. The change in the index determination process may involve the introduction of new weight values, which are appropriate for the new patient state.

Figure 8:
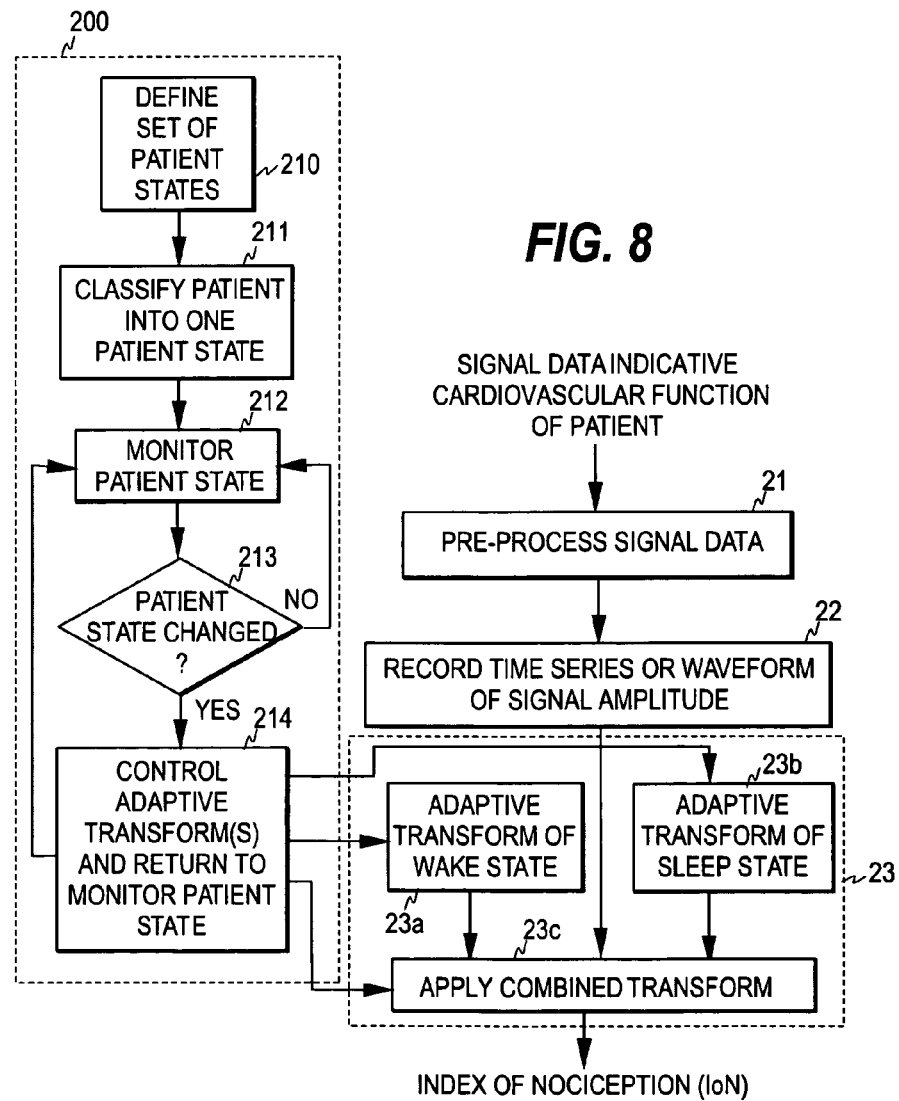
FIG. 8 illustrates a further embodiment of the invention, in which the transform applied to a physiological parameter is determined by the history data attached to the predefined patient state categories between which the current state of the patient is.

In still further embodiments of the invention, the clinical index is not determined based on one patient state category only, since the state of the patient may be somewhere between two patient state categories, whereby it is difficult to categorically classify the patient into one patient state category only. FIG. 8 illustrates how this may be implemented in connection with the embodiment of FIG. 3, in which only one parameter is utilized to calculate the clinical index. Since the transforms of the wake and sleep state categories are defined by different history data, they may be regarded as two different transforms, denoted with references 23a and 23b in FIG. 8. When the state of the patient is between two predefined patient state categories, the parameter(s) obtained from step 22, in this case signal amplitude, may be subjected to a transform which is produced as a combined transform from the transforms of the patient state categories between which the patient is (step 23c). Fuzzy logic may be employed to produce the combined transform, in which the two transforms may be weighted according to the current state of the patient. Thus, the more the patient moves towards the sleep state category, the more weight is given to the transform of the sleep state category. Similarly to the above, each transform in the embodiment of FIG. 1 may be divided into category-specific transforms, and some or all of the category-specific transforms may be used, depending on the current state of the patient, to produce a combined transform which is applied to the measurement signal (parameter) in question. The monitored state of the patient determines the category-specific transforms and their relative weights for producing the combined transform.

Figure 9:
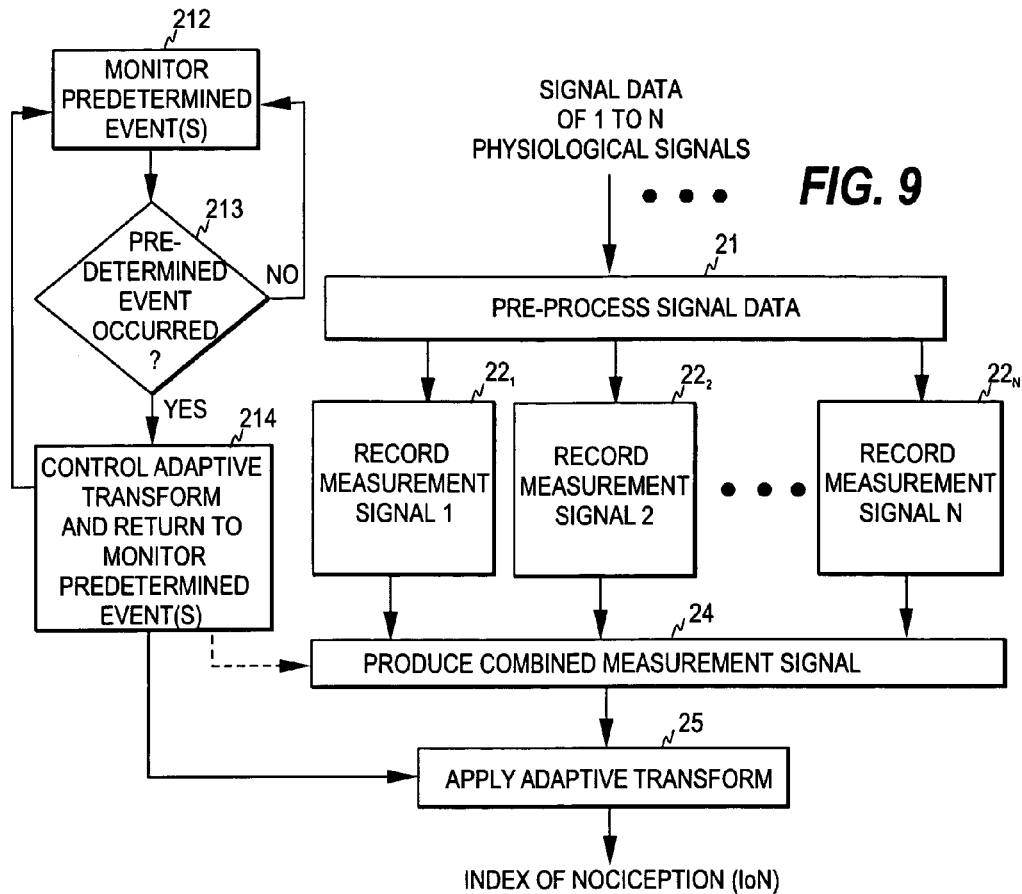
FIG. 9 illustrates a still further embodiment of the invention, in which several physiological parameters and only one adaptive transform are employed.

FIG. 9 illustrates a still further embodiment of the invention, in which at least two physiological parameters and only one adaptive transform is employed. In this embodiment, the order of the combinating step and the transform is changed by first producing a combined measurement signal based on the time series of at least two physiological parameters (step 24) and then subjecting the combined measurement signal to an adaptive transform (step 25). The output signal of the transform now serves as the diagnostic index indicative of the clinical state of the subject. If a predetermined event is detected at step 213, which indicates a change in the statistical properties of one or more of the physiological signals, the adaptive transform is controlled similarly as the parameter-specific transforms described above. When the adaptation mechanism is changed, the combinating step may also be controlled, as is indicated by a dashed arrow in the figure.

Figure 10:
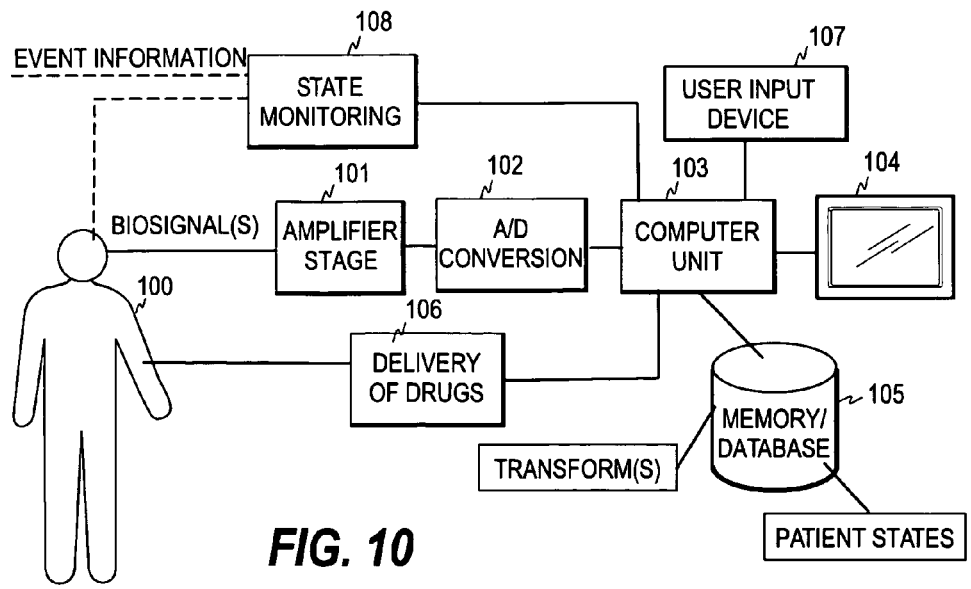
FIG. 10 illustrates one embodiment of a system according to the invention.

FIG. 10 illustrates one embodiment of the system or apparatus according to the invention. The physiological signal(s) obtained from one or more sensors attached to a patient 100 are supplied to an amplifier stage 101, which amplifies the signal(s) before they are sampled and converted into digitized format in an A/D converter 102. The digitized signals are supplied to a computer unit 103 which may comprise one or more processors.

The computer unit is provided with a memory or database 105 holding the digitized signal data obtained from the sensor(s). The computer unit may produce the time series needed, apply the transform to the selected time series, and determine the diagnostic index based on the transformed signal value(s). For this purpose, the memory may store the transforms to be used, and the adaptation parameters for each patient state category. Additional information affecting the selection of the adaptation parameters may be supplied through a user input device 107. The computer unit may define the patient state and thus also the corresponding state category based on the signal data obtained from the patient, or a separate monitoring unit 108 may be connected to the patient to notify the computer unit when the patient state category changes. The monitoring unit may also monitor the occurrence of a predetermined event in the clinical equipment used. In a further embodiment, no separate event monitoring is needed, but the anesthesiologist gives a notification of the change of the patient state category through the user input device.

Although one computer unit or processor may perform the above steps, the processing of the data may also be distributed among different units/processors (servers) within a network, such as a hospital LAN (local area network). The apparatus of the invention may thus also be implemented as a distributed system. However, implementing the apparatus as a compact monitoring unit which may be movable with the patient allows the monitoring of the patient to be continued in a post anesthetic care unit, for example.

The computer unit may display the results through at least one monitor 104 connected to the computer unit, and it may further supply the diagnostic index as input data to a device or system 106 delivering drugs to the patient, thereby enabling automatic control of the desired clinical state of the patient. For example, at least one analgesic may be delivered based on the index of nociception. The computer unit may act as a controlling entity controlling the administration of the drugs from the delivery system 106 to the patient. Alternatively, the computer unit may supply the diagnostic index to another computer unit or microprocessor (not shown), which then acts as the controlling entity controlling the drug delivery system 106. The said controlling entity is provided with the control data needed for the administration, such as the pharmacodynamic and pharmacokinetic properties of the drugs to be administered. The drug delivery system may comprise separate delivery units for one or more drugs to be administered, such as a delivery unit for an analgesic drug and/or a delivery unit for a hypnotic drug.

Figure 11:
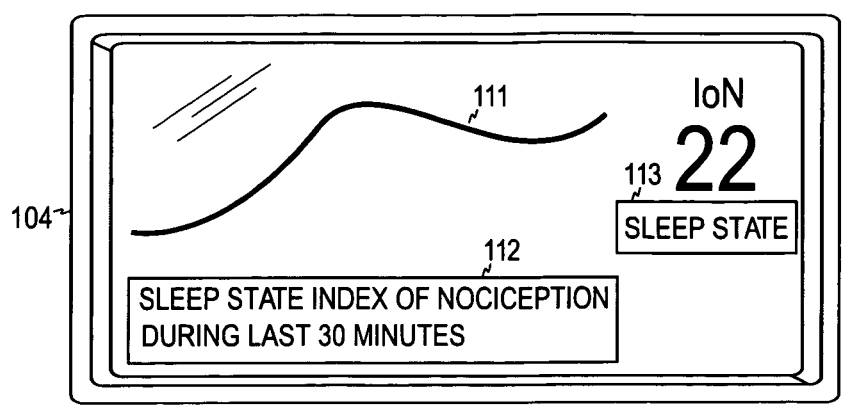
FIG. 11 illustrates an example of the visual indication of the clinical state of the subject.

Since the ANS of wakeful patients is more sensitive to additional factors, such as psychological stress, than the ANS of unconscious patients, the index values displayed may be accompanied with information indicating the patient state category with which the said values are associated. FIG. 11 illustrates one example of a monitor 114 displaying both the index curve 111 obtained during the last 30 minutes and the numeric value of the current index. The information indicating the patient state category for which the curve and the current value are measured may be given in one or more separate message fields 112 and 113, for example. Different colors may also be used for indices of different categories.

A conventional measurement device, such as a pulse oximeter, may also be upgraded to enable the device to determine the diagnostic index in the above-described manner based on the signal data that the device measures from the patient. Such an upgrade may be implemented by delivering to the measurement device a software module that enables the device to determine the diagnostic index in the above-described manner. The software module may be delivered, for example, on a data carrier, such as a CD or a memory card. The software module, which is provided with an interface to the memory storing the signal data measured by the measurement device, may use the said signal data to determine the patient state category to which the patient belongs and it may apply any of the above-described transforms to the signal data to determine the diagnostic index.

It is also possible that a measurement device in which the determination of the diagnostic index is based on one or more transformed signals is upgraded by introducing a software module that makes the transforms already in use dependent on the categories into which the patient may be classified based on his/her current state.

Although the invention was described above with reference to the examples shown in the appended drawings, it is obvious that the invention is not limited to these, but may be modified by those skilled in the art without departing from the scope and spirit of the invention. For example, several predetermined events may be monitored to detect the transitions between two patient state categories. It is also possible to apply an additional transform to the weighted average calculated based on the transformed signals. Furthermore, different transforms may be applied to different parameters, at least one parameter may be transformed in more than one way, or the adaptive transforms may be applied to only some of the physiological parameters.

The invention claimed is:

1. A method for providing a diagnostic index that is indicative of a clinical condition of a subject when the subject is in either of a pair of subject states and during a transition period following a change in the state of the subject from a first subject state to a second subject state, the changeable state of the subject being defined by different physiological characteristics of the subject than the clinical condition of the subject for which the diagnostic index is being provided, the method comprising the steps of:
  (a) obtaining a first signal using one or more sensors coupled to the subject, said first signal being responsive to the physiological functioning of an organ or organs of a first anatomical system of the subject, said first signal being capable of indicating the state of the subject;
  (b) acquiring at least one second signal from one or more sensors coupled to the subject to provide at least one clinical condition indicating signal, the second signal being responsive to the physiological functioning of an organ or organs of a second anatomical system of the subject different than the first anatomical system, the clinical condition indicating signal having at least one property that can be altered by a change in the state of the subject;
  (c) providing at least one adaptive transform in a computer unit for transforming an input signal applied thereto an outputted, transformed signal in accordance with an alterable, signal transforming characteristic of the adaptive transform;
  (d) with the subject in a first state, obtaining clinical condition indicating signal history data from the subject;
  (e) extracting statistical feature data from the clinical condition indicating signal history data;
  (f) using the statistical feature data to establish the signal transforming characteristic of the adaptive transform to one that transforms an input signal to an outputted, transformed signal having desired value range and distribution characteristics for the first state of the subject;
  (g) applying the clinical condition indicating signal as the input signal to the adaptive transform to provide a transformed signal for the first state of the subject from the adaptive transform;
  (h) forming, from the transformed signal, a diagnostic index in a form capable of perception to provide an indication of the clinical condition of the subject for the first state of the subject;
  (i) obtaining statistical feature data characterizing clinical condition indicating signal data for a second state of the subject;
  (j) determining a change in the state of the subject using the first signal;
  (k) upon the occurrence of a change in the state of the subject to a second state, replacing at least a portion of the statistical feature data for the first state used to establish the signal transforming characteristic of the adaptive transform with statistical feature data obtained in step (i)

to alter the signal transforming characteristic of the adaptive transform to one that transforms the clinical condition indicating input signal to an outputted, transformed signal having desired value range and distribution characteristics for forming the diagnostic index as an indication of the clinical condition of the subject in a transition period following change of the subject from the first state to the second state;

(l) with the subject in the second state, extracting statistical feature data from clinical condition indicating signal history data obtained from the subject in the second state; and (m) replacing at least a portion of the statistical feature data obtained in step (i) with statistical feature data extracted in step (l) to further alter the signal transforming characteristic of the adaptive transform so that the diagnostic index formed from the transformed signal continues as a indication of the clinical condition of the subject in the second state.

2. The method according to claim 1 wherein step (i) is further defined as previously obtaining clinical condition indicating signal history data for the subject in the second state and extracting statistical feature data from the previously obtained clinical condition indicating signal history data for the subject in the second state.

3. A method according to claim 1 wherein step (i) is further defined as obtaining clinical condition indicating data from a group of subjects and extracting statistical feature data from the subject group clinical condition indicating data.

4. A method according to claim 3 wherein step (k) is further defined as decreasing the degree to which the signal transforming characteristic of the adaptive transform is based on statistical feature data obtained from subject group clinical condition indicating data and increasing the degree to which the adaptive transform is based on statistical feature data extracted from clinical condition indicating signal history data obtained from the subject following a change in the state of the subject.

5. A method according to claim 1 wherein step (b) is further defined as providing at least two clinical condition indicating signals, steps (c), (d), (e), (f), (g), (i), (k), (l), and (m) are carried out for each of the clinical condition indicating signals, and step (h) is further defined as forming the diagnostic index from the at least two transformed signals.

6. The method according to claim 5 wherein step (h) is further defined as forming the diagnostic index as a weighted average of the at least two transformed signals.

7. The method according to claim 6 further including the step of altering the weighting of the transformed signals forming the diagnostic index when the subject state of the subject changes.

8. A method according to claim 1 wherein step (b) is further defined as providing two clinical condition indicating signals and combining the clinical condition indicating signals, and step (g) is further defined as applying an input signal to the adaptive transform comprising a combined clinical condition indicating signal.

9. The method according to claim 1 wherein step (c) is further defined as providing an adaptive transform for each of the states of the subject and including the step of forming a combined adaptive transform from the adaptive transform for each state and wherein in step (g) the clinical condition indicating signal is applied to the combined adaptive transform.

10. The method according to claim 9 wherein in the step of forming a combined adaptive transform, the adaptive transforms for each state are weighted according to the existing state of the subject.

11. A method according to claim 1 further comprising a step of displaying the diagnostic index in a display unit, in which the displaying step includes displaying visual information identifying the state of the subject.

12. A method according to claim 1 wherein step (a) is further defined as obtaining a first signal capable of indicating a wake state in which the subject is conscious and a sleep state in which the subject is unconscious, wherein step (b) is further defined as acquiring at least one second signal for providing a clinical condition indicating signal indicative of the nociceptive condition of the subject, and wherein the diagnostic index forming steps comprise forming the diagnostic index as an indication of the nociceptive condition of the subject.

13. The method according to claim 1 wherein step (a) is further defined as obtaining a first signal responsive to the physiological functioning of the brain of the nervous system of the subject.

14. The method according to claim 1 wherein step (b) is further defined as acquiring at least one second signal responsive to the physiological functioning of an organ in the cardiovascular system of the subject.

15. The method according to claim 13 wherein step (b) is further defined as acquiring at least one second signal responsive to the physiological functioning of an organ in the cardiovascular system of the subject.

16. A method for providing a diagnostic index indicative of the nociceptive condition of a subject when the subject is in either of a pair of subject states relating to the hypnotic wake-sleep state of the subject and during a transition period following a change in the state of the subject from a wake state to a sleep state, the method comprising the steps of:

(a) obtaining a first signal using one or more sensors coupled to the subject, said first signal being responsive to the cortical functioning of the subject and being capable of indicating the wake-sleep state of the subject;

(b) acquiring at least one second signal from one or more sensors coupled to the subject to provide at least one nociceptive condition indicating signal, the second signal being responsive to the subcortical functioning of the subject, the nociceptive condition indicating signal having at least one property that can be altered by a change in the state of the subject;

(c) providing at least one adaptive transform in a computer unit for transforming an input signal applied thereto an outputted, transformed signal in accordance with an alterable, signal transforming characteristic of the adaptive transform;

(d) with the subject in the wake state, obtaining nociceptive condition indicating signal history data from the subject;

(e) extracting statistical feature data from the nociceptive condition indicating signal history data;

(f) using the statistical feature data to establish the signal transforming characteristic of the adaptive transform to one that transforms an input signal to an outputted, transformed signal having desired value range and distribution characteristics for the wake state of the subject;

(g) applying the nociceptive condition indicating signal as the input signal to the adaptive transform to provide a transformed signal for the wake state of the subject from the adaptive transform;

(h) forming, from the transformed signal, a diagnostic index in a form capable of perception to provide an indication of the nociceptive condition of the subject for the wake state of the subject;

(i) obtaining statistical feature data characterizing nociceptive condition indicating signal data for a sleep state of the subject;
(j) determining a change in the state of the subject from the wake state to the sleep state using the first signal;
(k) upon the occurrence of a change in the state of the subject to the sleep state, replacing at least a portion of the statistical feature data for the wake state used to establish the signal transforming characteristic of the adaptive transform with statistical feature data obtained in step (i) to alter the signal transforming characteristic of the adaptive transform to one that transforms the nociceptive condition indicating input signal to an outputted, transformed signal having desired value range and distribution characteristics for forming the diagnostic index as an indication of the nociceptive condition of the subject in a transition period following change of the subject from the wake state to the sleep state;
(l) with the subject in the sleep state, extracting statistical feature data from nociceptive condition indicating signal history data obtained from the subject in the sleep state; and
(m) replacing at least a portion of the statistical feature data obtained in step (i) with statistical feature data extracted in step (l) to further alter the signal transforming characteristic of the adaptive transform so that the diagnostic index formed from the transformed signal continues as an indication of the nociceptive condition of the subject in the sleep state.

\* \* \* \* \*